United States Patent [19]

Olson et al.

[11] Patent Number: 5,311,290
[45] Date of Patent: May 10, 1994

[54] IMAGING APPARATUS AND METHOD OF FIBER ANALYSIS

[75] Inventors: James Olson; Andrew G. Robertson; Timothy D. Finnigan, all of Vancouver, Canada

[73] Assignees: Pulp and Paper Research Institute of Canada, Pointe Claire; University of British Columbia, Vancouver, both of Canada

[21] Appl. No.: 953,623

[22] Filed: Sep. 30, 1992

[51] Int. Cl.$^5$ .............................................. G01B 11/04
[52] U.S. Cl. ................................... 356/383; 356/238; 356/246; 348/142
[58] Field of Search ............... 356/383, 238, 246, 335, 356/336; 358/107

[56] References Cited

U.S. PATENT DOCUMENTS

| | | | |
|---|---|---|---|
| 3,816,001 | 6/1974 | Duncan et al. | 356/383 |
| 4,266,874 | 5/1981 | Janin et al. | 356/335 |
| 4,352,558 | 10/1982 | Eisert | 356/336 |
| 4,460,921 | 7/1984 | Henry et al. | 358/107 |
| 4,737,648 | 4/1988 | Smith et al. | 356/343 |
| 4,792,233 | 12/1988 | Irvine | 356/440 |
| 4,887,155 | 12/1989 | Massen | 358/107 |
| 4,926,350 | 5/1990 | Bechtel et al. | 364/550 |
| 4,963,035 | 10/1990 | McCarthy et al. | 382/28 |
| 4,983,038 | 1/1991 | Ohki et al. | 356/246 |

FOREIGN PATENT DOCUMENTS

| 1176839 | 10/1984 | Canada . | |
|---|---|---|---|
| WO91/14169 | 9/1991 | PCT Int'l Appl. | 356/238 |

OTHER PUBLICATIONS

A Simple Rapid Method for Determining Fiber Dimensions Abbot, Jaycox & Ault, The Proctor and Gamble Company pp. 119 to 132, 1979.
High Resolution DNA Content Measurements of Mammalian Sperm—Authors: Pinkel et al pp. 1–9 Cytometry vol. 3, No. 1, 1982.
Application of Image Analysis of Pulp Fibre Characterisation Authors: Jord & Page—Pulp and Paper Institute of Canada pp. 745–765, Transactions of Symposium 1981 Published 1983 by Mech. Eng. Publications Ltd.
Flow Cytometry-Author: Steinkamp pp. 1375–1400 Rev. Sci. Instrum. 55(9) Sep. 1984.
Curl, Crimps, Kinks & Microcompressions in Pulp Fibres Authors: Page, Seth, Jordan & Barbe-Pulp & Paper Research Institute of Canada pp. 183–227 Transactions of Symposium Sep. 1985 Published: Mech. Eng. Publications Ltd.
Curvature Kink and Curl Authors: Jordan & Nguyen pp. 313–318 Paperi JA PUU-Papper Och Tra Apr. 1986.
Fiber-Optic Flocculation Sensor for On-Line Control . . . Authors: Eisenlauser, Horn, Linhart & Hemel—BASF pp. 132–138 Nordic Pulp and Paper Research Journal Apr. 1987.
Continuous On-Line Measurement of Dirt and Shives Author: Predmore, Phoenix Tech. Inc. pp. 237–247 Tappi Proceeding 1989 Pulping Conference.
Fibre Deformation and Its Implictations in Pulp Characterization Authors: Mohlin & Alfredsson pp. 172–179 Nordic Pulp & Paper Research Journal No. 4/1990.
Curvature Measurement in a Network of Crossing . . . Authors: Nguyen & Jordan pp. 375 to 381–1991 International Paper Physics Conference Tappi Press 1991.

*Primary Examiner*—F. L. Evans

[57] ABSTRACT

A method and apparatus for positioning, aligning and orienting fibers in flowing fluids, to permit fibers such as wood pulp fibers to be accurately imaged and rapidly measured with little operator involvement, utilizing a plugging resistant and fouling resistant sheath flow cell, is described. An embodiment is disclosed which simultaneously determines the distributions of shape (curl) and length of samples of wood pulp fibers. Fibers are transported in a dilute water suspension through a sheath flow cell that orients fibers normal to an imaging system that includes a two-dimensional CCD video camera. Images of fibers are analyzed rapidly by a processor, which calculates the shape and length of individual fibers. The data are displayed on a cathode ray tube screen while a pulp sample is being analyzed, and are stored in processor memory for further analysis.

25 Claims, 7 Drawing Sheets

IMAGING APPARATUS AND METHOD OF FIBER ANALYSIS

TECHNICAL FIELD

The present invention relates to analysis of fibers and more specifically to a rapid method for determining the effects of mechanical treatment on pulp fibers.

BACKGROUND ART

In pulping and paper making, pulp fibers receive mechanical treatment which affects properties such as fiber length, deformation, flexibility and external fibrillation. This also affects the mechanical, structural and optical properties of sheets made from the fibers. Refining is a key step in optimizing pulps during paper making and has a number of effects on the fibers. For example refining enhances fiber-to-fiber bonding which strengthens a sheet but lowers its opacity. The refining step can also cut fibers to reduce fiber flocculation. It also deforms fibers by creating local defects in fiber walls which increases the wet web stretch but lowers the dry sheet elastic modulus.

Pulp properties such as fiber deformation and length can be changed by mechanical treatment and are distributions for a fiber population. During mechanical treatment several such property distributions change simultaneously. Instrumentation is needed which can determine on a fiber-by-fiber basis the values of more than one pulp property such as fiber length, fiber deformation and fiber flexibility. With regard to deformation, there are different measures of fiber deformation including curl and kink indices and mean and local fiber curvature. These different measures correlate to sheet properties in different ways.

Rapid measurements of fiber properties other than deformation have been made by transporting large numbers of fibers through a flow cell, past an imaging detector or photodetector. In some cells, large numbers of fibers pass through a cell at high fiber concentrations so test results are based on groups or flocs of fibers and are not fiber-by-fiber. Capillary cells are often used for fiber-by-fiber analysis. Such cells align and position each fiber but are subject to fiber clogging. Other types of cells are known for measuring fiber length and width but these cells are subject to fouling wherein resins, dirt and other chemicals present in the suspension with the fibers are deposited on the inside walls of the cell.

Sheath type flow cells wherein a liquid containing the particles to be analyzed is injected into a sheath liquid, have been used in biomedical research and also for plankton analysis but such cells are not suitable for rapidly measuring fiber length and fiber deformation in high aspect ratio fibers because such cells do not orient the fibers with a planar deformation. This does not permit a two dimensional imaging detector to reliably image a fiber, particularly one that is non-oriented.

Fiber diameter has been rapidly measured in non-imaging systems with a non-sheath type flow cell. Such cells that are thick enough to be plug resistant do not constrain fibers to a thin enough region for imaging systems to focus effectively on all fibers which results in unreliable measurements of fiber deformation and fiber length.

Although many commercial image analyzers and dedicated imaging systems are widely used for industrial inspection, some of which characterize the shape of a linear feature in a two dimensional image, none of the systems is capable of measuring the deformation or length of small deformed fibers such as pulp fibers.

DISCLOSURE OF INVENTION

The present invention provides first of all a rapid and accurate imaging fiber analyzer apparatus to overcome the problems discussed. In one embodiment, the invention includes a sheath type flow cell device and a method for determining fiber length. In another embodiment, the sheath type flow cell device measures the distribution of fiber deformation as well as the fiber length in pulp and paper making furnishes. This enables the effects of mechanical treatment on pulps to be determined. The device in a further embodiment determines flexibility properties of fibers.

One aim of the present invention is to provide a sheath type flow cell device for an imaging fiber analyzer to axially align, orient and position curved high aspect ratio fibers into a plane parallel to the flow direction and normal to an imaging system which provides accurate fiber length and shape measurements for individual fibers. The cell when used with an imaging fiber analyzer is able to provide simultaneous multiparameter measurements on a fiber-by-fiber basis.

A further aim is to provide a sheath type flow cell device for an imaging fiber analyzer which orients fibers in order that fiber length and shape measurements made on projected two dimensional images of individual fibers have reliable visual contrast. For non-birefringent fibers, it is necessary to first dye the fibers. For birefringent fibers, crossed circular polarizing filters may be used. A still further aim of the present invention is to provide a sheath type flow cell device for imaging fiber analyzers which resists plugging by fibers, fiber bundles, flocs and shives and also resists fouling by resins and other components typical of industrial pulp furnishes.

A still further aim of the present invention is to provide sheath type flow cells suitable for determining length, deformation and flexibility properties of fibers. The flow cell may be suitable for determining length properties only, length and deformation properties only, or length, deformation and flexibility properties of fibers. In one embodiment, the sheath type flow cell is a high speed flow through cell that may be used on-line for control in pulp refiners.

The present invention provides a fiber analyzer for determining fiber lengths of fibers in a fiber suspension, comprising: a flow cell having a first flow passage for a fiber suspension sample stream with at least one sheath flow passage about the first flow passage, the first flow passage tapering to an exit aperture connecting with the sheath flow passage to form a combined passage, the combined passage having a reduction in area downstream of the exit aperture to align and position fibers in a thin elongated stream; an imaging area in the cell downstream of the reduction in area in the combined passage, wherein the elongated stream is surrounded by sheath fluid, a light source to apply light to one side of the imaging area in the cell, an imaging detector on an opposite side of the imaging area to the light source, the imaging detector providing signals representing fiber present in the imaging area, and means to process the signals to determine fiber length.

In a further embodiment the flow cell guides the fiber suspension stream into an elongated planar stream to align, position and orient the fibers thus permitting the imaging detector to provide signals that may be processed to determine fiber deformation as well as fiber length. In a still further embodiment there is provided a fiber analyzer having a shear area within the imaging area, images of fibers are taken in the fiber suspension stream before passing into the shear area and while in the shear area to produce signals that are processed to determine fiber flexibility as well as fiber length.

In a still further embodiment there is provided a method of determining fiber length for fibers in suspension comprising the steps of passing a fiber suspension stream through a sheath type flow cell wherein the fiber suspension stream is injected into a sheath fluid stream to align and position fibers and form an elongated combined stream, projecting light from one side of the combined stream, collecting an image of fibers in the stream on an opposite side from the light and producing signals representative of fiber images, and processing the signals to determine fiber length.

In further embodiments the fiber suspension stream within the sheath fluid is an elongated planar stream with fibers aligned, positioned and oriented, and signals collected from the images of fibers are processed to determine fiber length and fiber deformation.

In a still further embodiment a shear area is included within an imaging area, images are taken of fibers before the shear area and in the shear area and signals are produced comparing the different images of fibers, showing how they flex to determine an indication of fiber flexibility.

BRIEF DESCRIPTION OF DRAWINGS

In drawings which illustrate embodiments of the present invention.

MODES FOR CARRYING OUT THE INVENTION

Figure 1:
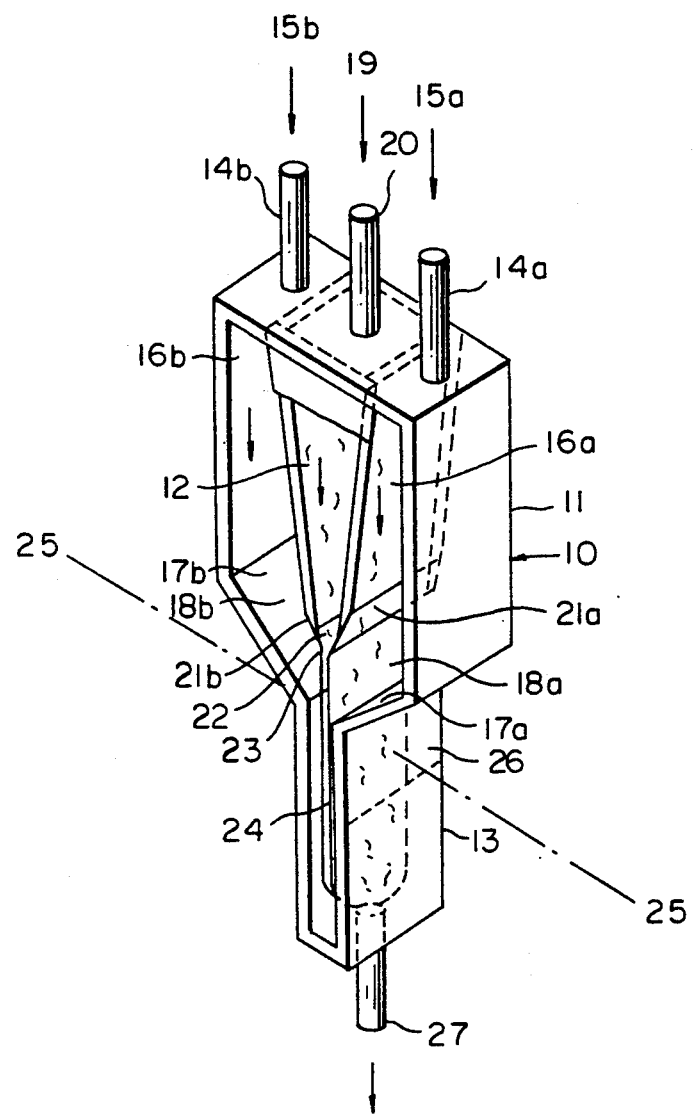
FIG. 1 is a schematic perspective view showing one embodiment of a sheath type flow cell according to the present invention.
Figure 3:
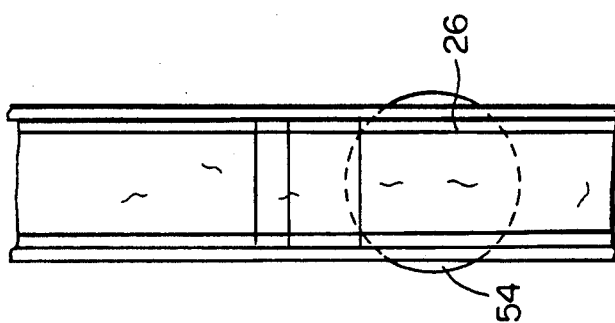
FIG. 3 is a sectional view taken at line 3—3 of FIG. 2.
Figure 2:
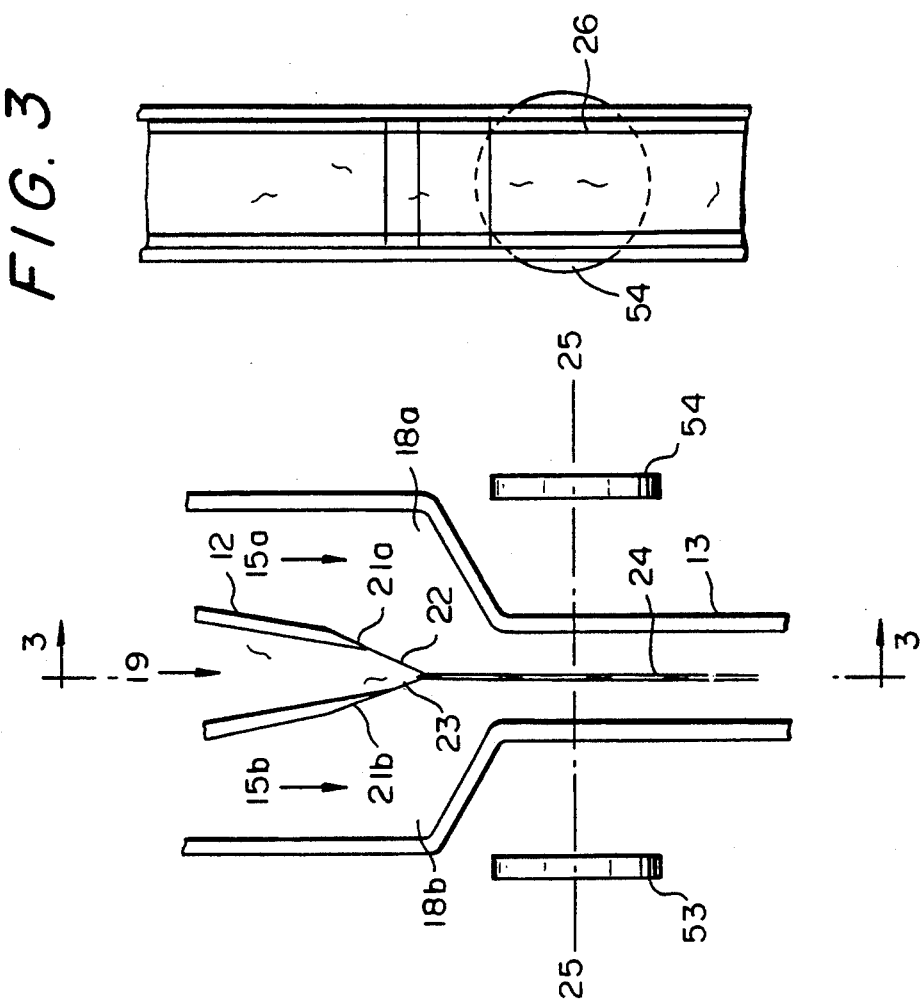
FIG. 2 is a diagrammatic side view showing the flow cell of FIG. 1.

One type of sheath type flow cell is shown in FIGS. 1 to 3 wherein the flow cell 10 is essentially a rectangular duct with a wide initial sheath fluid passage 11 for sheath fluid, preferably water, and inside the sheath fluid passage 11 is a first passage 12 for a fiber suspension stream. An imaging area duct 13 is positioned downstream of the sheath flow passage 11 and the sample passage 12.

The flow cell includes two inlets 14a and 14b for sheath fluid 15a and 15b, preferably water, which feed into two substantially rectangular flow passages 16a and 16b. The sheath fluid passages 16a and 16b extend downwards to tapered surfaces 17a and 17b in the outside of the cell, to provide outlets 18a and 18b so the sheath fluid joins about the exit of the first passage 12 leading into the imaging area duct 13.

A dilute fiber suspension stream 19 enters through an inlet 20 into the first passage or sample passage 12, a longitudinal slit 22 is provided at the end of the first passage 12, the side walls of the first passage 12 having tapered ends 21a and 21b. The dimensions of the slit 22 are large enough that fibers, fiber bundles and flocs, and shives typical of industrial mill furnishes do not plug the cell. The fiber suspension stream 19 passes through the longitudinal slit 22 of the first passage 12 and the sheath fluid joins smoothly to the outside of the fiber suspension stream to form a narrow elongated planar fiber suspension stream 24 between two streams of sheath fluids. As the sheath fluids join the fiber stream, they have centrally directed transverse velocity components generated by the tapered surfaces 17a and 17b of the cell 10. They may also have a higher velocity. The sheath fluids entrain the fiber stream, accelerating and reducing the thickness of the fiber stream in the tapered region 23 just downstream of the longitudinal slit 22 to form a combined stream. The imaging area duct 13 is oriented such that the resulting thin elongated planar fiber suspension stream 24 is normal to an optical axis 25 of the imaging system. The imaging area 26, shown in FIG. 3, is constructed of a flat transparent non-birefringent material such as glass or Plexiglass that allows coupling to an imaging fiber analyzer. The combined stream exits through the downstream discharge port 27.

The fiber suspension stream 19 exiting from the longitudinal slit 22 is entrained and compressed toward the central plane by the faster moving sheath fluids 15a and 15b which pass through flow passages 18a and 18b. The fiber stream tapers smoothly to an elongated planar stream 24 normal to the imaging axis 25. In the tapered region 23, planar deformed fibers are gradually oriented within the stream by the centrally directed transverse velocity components imposed by the sheath fluids and tend to be axially aligned by the elongating flow created by the tapered surfaces 17a and 17b. High aspect ratio fibers with substantially planar deformation, lie in a plane normal to the imaging axis 25.

Figure 4:
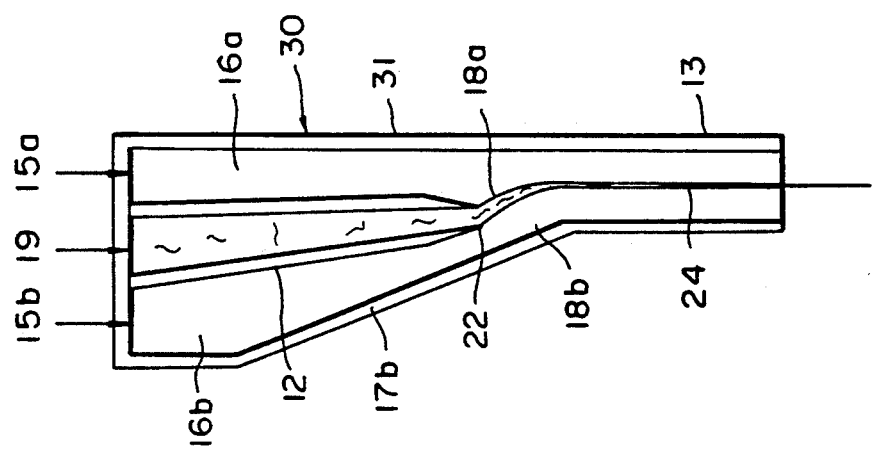
FIG. 4 is a diagrammatic side view of a flow cell according to another embodiment of the present invention.

A further embodiment of a flow cell is shown in FIG. 4 wherein the cell 30 has all the components shown in cell 10 but is asymmetric. The wall 31 on the imaging detector side is flat and only one sheath flow passage 18b being tapered by tapered wall 17b. The other sheath flow passage 18a is essentially a smoothly tapered duct with the first passage 12 being at an angle forming a shallow taper. This modification improves the performance of the imaging fiber analyzer by allowing the imaging optical system to be closer to the flow cell and have a higher magnification. This increases the accuracy and reliability of the image processing and of the resulting fiber measurements.

Figure 5:
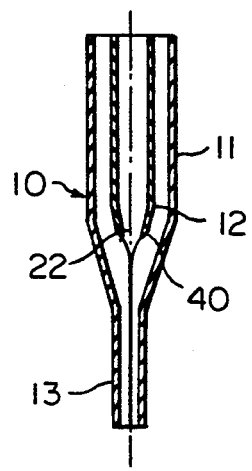
FIG. 5 is a sectional view through a further embodiment of a flow cell according to the present invention.

FIG. 5 shows a sheath type flow cell 10 suitable for measuring fiber length rapidly on a fiber-by-fiber basis in either bench or on-line configurations. The first sample passage 12 has a circular cross-section with a frusto-conical end 40 leading to a circular opening 22, which forms an injector. Thus the cell 10 has a fiber suspension stream passing down the inner tube 12 where it is injected into a sheath fluid stream within the outer casing or sheath flow passage 11. At the particular point of injection, the outer casing 11 is tapered to a smaller diameter (by a frusto-conical portion), representing the imaging area duct 13. This duct 13 has a constant cross-sectional area for the length of the imaging area. The size of the circular opening 22 and the duct 13 is sufficient to avoid plugging by shives or fibers.

Figure 6:
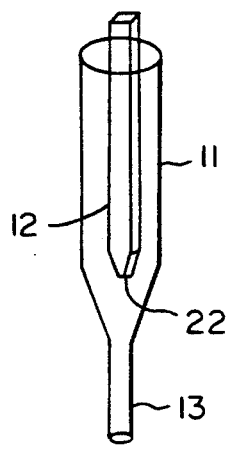
FIGS. 6 and 7 are schematic perspective views of further embodiments of a sheath type flow cells.
Figure 7:
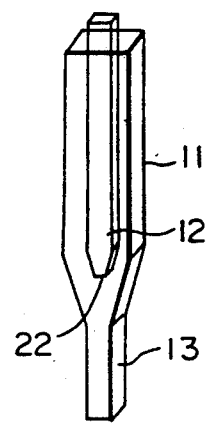

FIG. 6 illustrates another embodiment which, like FIG. 1, has a coaxial shape with the fiber suspension first passage 12 being rectangular in cross-section and ending with a longitudinal slit 22. FIG. 7 shows a further embodiment wherein the sheath flow passage 11 has a rectangular cross-section as opposed to a circular cross-section shown in FIG. 6. The imaging area duct 13 in FIG. 6 has a circular cross-section and in FIG. 7 has a rectangular cross-section. By providing a rectangular taper, rather than a circular or square taper, leading to the longitudinal slit 22 as shown in FIGS. 6 and 7, as opposed to a circular opening as shown in FIG. 5, the fibers are positioned, aligned and oriented and this enables the fibers to pass through the imaging area duct 13 with deformed fibers oriented in such a manner that the length and deformation of the fibers can be imaged with minimal projection errors. In the case of the cell shown in FIG. 5, the fibers are aligned and positioned but not necessarily oriented and therefore one obtains a true reading on length of straight fibers only. If required, fibers can be straightened by a hot disintegration step before imaging occurs. A single dimension imaging detector can be used for the cell shown in FIG. 5 which provides fast information cheaply.

Figure 8:
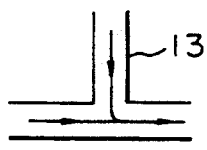
FIGS. 8, 9, 10 and 11 are diagrammatic views of shear areas in imaging areas of a flow cell according to other embodiments of the present invention.

By utilizing the flow cells shown, one is able to obtain information relating to fiber length and fiber deformation. However, by inserting a shear area into the fiber imaging duct 13, and using a fluid with an appropriate viscosity, one is able to determine fiber flexibility as well as the other two parameters. FIG. 8 shows the imaging area duct 13 extending to a T-shape wherein a stream of fluid is provided from one end of the T-shape causing the fiber suspension stream to turn through 90°. This turn forms a shear area and by imaging fibers prior to the turn and while in the turn one is able to identify how the fiber changes its shape which in turn provides an indication of fiber flexibility.

Figure 9:
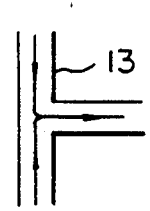
Figure 10:
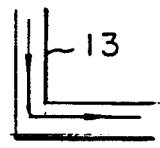
Figure 11:
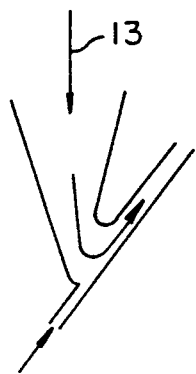

FIG. 9 shows another embodiment of a shear area wherein the T-shape is the other way around with a fluid forced up from underneath to cause the fiber stream to turn through 90°. FIG. 10 shows an elbow which again causes the fiber stream to turn through 90° and FIG. 11 shows a tapered V-bend in the imaging area duct 13 which causes the fibers in the fiber stream to flex as they accelerate in the taper and then pass around the bend. A fluid enters the V-bend to create more shear. Thus by imaging the fibers before entering the shear area and while in the shear area, one is able to determine flexibility of the fibers.

Figure 12:
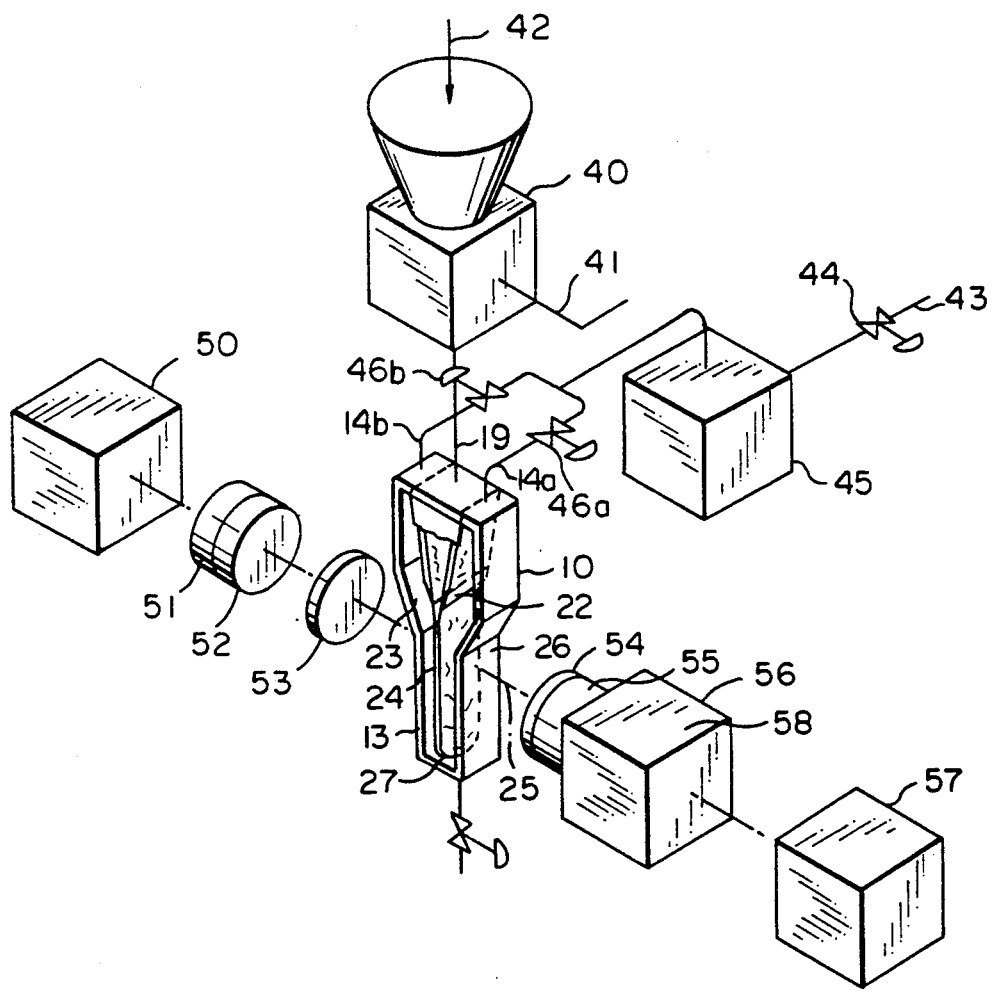
FIG. 12 is a schematic exploded perspective view of an embodiment of an imaging fiber analyzer according to the present invention.

FIG. 12 shows the flow cell 10 with a sample reservoir 40 positioned thereabove. A gentle agitation 41, preferably a compressed air bubbler, is provided in the reservoir 40 into which a dilute fiber bearing sample suspension 42 is introduced. The fiber suspension 42 is fed into the sample fluid inlet 19 of the flow cell device 10. A pump delivers clean sheath fluid, which is preferably water, to the sheath inlets 14a and 14b of the flow cell 10. In the embodiment shown a supply of compressed air 43 and pressure regulator 44 maintains a constant low pressure inside a water containing pressure vessel 45. This forces a smooth pulse-free stream of water through two control valves 46a and 46b to the sheath fluid inlets 14a and 14b. Variation of the flow valves allows control over the flow rates and velocities and controls the thickness and position of the elongated planar stream 24 of fiber suspension.

The optical system comprises a light source 50 on one side of the flow cell 10 from which light passes through a diffuser 51 and condenser 52 to ensure that the imaging area 26 of the flow cell 10 receives even illumination. Light passes through a first circular polarizer 53 and then through the imaging area 26 of the flow cell 10, through a second circular polarizer 54 which is in the extinction position with respect to the first polarizer 53. The light then passes through an imaging lens 55 with a low power magnification to reach a two dimensional imaging detector 56. Signals from the detector 56, representing the detected image, are processed by at least one processor 57. The processor 57 detects when a fiber is present in the image region 26 of the flow cell device and determines the location of the centerline of the detected fiber image and determines the length and shape of the fiber centerline. The measurements for each imaged fiber are stored in electronic memory for later use.

For non-birefringent fibers that are non-opaque, the fibers are dyed to generate visual contrast and polarizers are not required. For birefringent fibers, polarizing filters generate a visual contrast and dyeing is unnecessary. When no fiber is present no light reaches the detector. When a fiber is imaged and is lying substantially in a plane normal to the optical axis 25, it is imaged by the detector 56 as a bright object. Stop-motion images are generated, typically by an electronic shutter 58 in the detector 56 as the fiber moves through the imaging area 26.

Figure 13A:
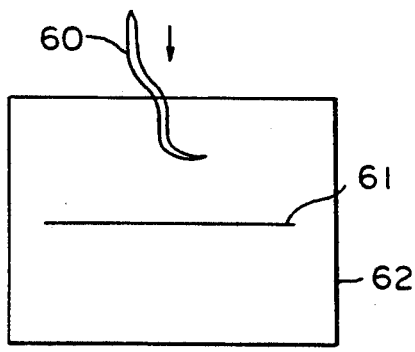
FIG. 13a to 13f are schematic representations illustrating fibers in the imaging area of a sheath type flow cell.
Figure 13D:
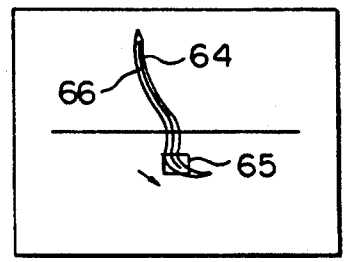
Figure 13B:
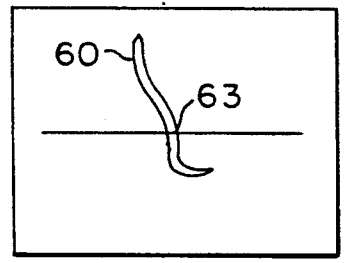
Figure 13E:
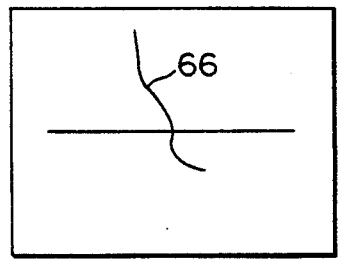
Figure 13C:
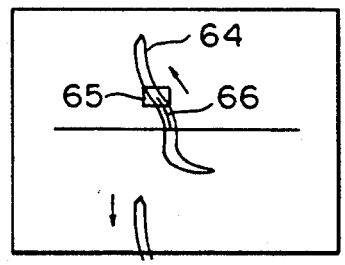

Image processing and analysis to calculate fiber shape and length are made rapid utilizing a standard video rate image system on known inexpensive hardware. If more rapid imaging is needed, then higher rates of imaging can be used. Image processing for fiber detection is separated from image processing for fiber analysis and measurement in order to minimize the number of calculations the processor must do both to detect a fiber and to process and analyze a detected fiber. Referring to FIG. 13, a fiber 6C is not detected in FIG. 13a and is only detected when the fiber 60 crosses the detection line 61 which represents a single row of pixels in the image area 62. This line 61 is at right angles to the flow direction and roughly central in the image area depending on the flow rate and frame rate. The detection line 61 is positioned to ensure that all fibers when detected are completely within the image. As shown in FIG. 13b the processor detects a fiber 60 on line 61 at pixel 63. The processor then acquires an image of the fiber 64, and traces or tracks the fiber centerline 66 rapidly by restricting its calculations to pixels 65 near or local to the fiber itself both above line 61 and below line 61 as shown in FIGS. 13c and 13d. The processor determines the fiber centerline 66 as shown in FIG. 13e and this is measured for deformation and length.

During image analysis, fiber detection processing is inactivated so that other fibers are not analyzed at the same time and this prevents any fiber from being detected more than once.

Figure 13F:
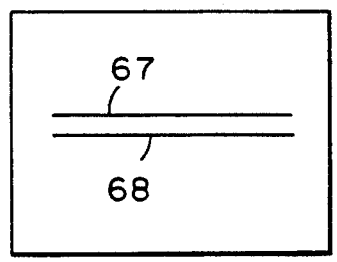

Two detection lines 67 and 68 are shown in FIG. 13f to ensure that short fibers do not pass through the imaging area without being analyzed. In certain cases more than two scan lines may be provided. As stated the imaging occurs at 1/30 second per image, being a standard video rate image system, and therefore the speed of fibers past the imaging lines is determined to ensure that short fibers are caught by at least one scan line.

When crossed fibers are encountered in the image the local centerline tracker 63 tends to trace a single fiber through a crossing which results in crossed fiber algorithms and related problems being avoided. Error detecting provisions are built in to the tracking algorithm such that if the tracker makes an error, the data for that image are discarded.

In many fibers, the fiber tracker encounters fiber segments that have poor visual contrast. These occur unpredictably at kinks and fiber ends and the tracker is able to distinguish between the two cases and react appropriately. While the fiber orienting ability of the flow cell minimizes loss of visual contrast at kinks, low fiber image contrast at a kink is bridged by the tracker when it is encountered and is not interpreted as a gap between two short fibers. For this, when it encounters low contrast, the tracking algorithm searches some distance ahead of the current end of the traced fiber centerline looking for another adjacent fiber segment. Suspension dilution minimizes the chance of a second fiber being close enough to be mistakenly interpreted as an adjacent segment of a continuous fiber.

When a shear are is incorporated into an imaging area, a flow cell 10, such as that shown in FIGS. 1, 6 and 7, orients, aligns and positions fibers on entry and permits the flow cell to control closely how an arbitrarily deformed fiber enters a shear area so that (1) all fiber deformations can be imaged with minimal projection errors, (2) both the bending moments applied to the fiber by the shear flow field and the resulting change in deformation are in the same plane as the initial fiber deformation, and (3) the paths fibers take through the shear field are relatively constant between fibers and can be controlled to be at the optimum location within the shear area. These factors assist in the process of calculating accurate fiber flexibilities. By analyzing the image of the fiber just before it enters the shear area, the processor calculates the fiber length and relaxed shape or curl. By analyzing a series of images acquired while the fiber passes through the shear region the processor calculates the fiber flexibility. By measuring the local curvature changes along each fiber the processor distinguishes longer fiber segments that bend smoothly like elastic beams from short weakened regions that bend like hinges. By this, the processor generates a more detailed desertion of the flexibility distribution for a fiber and a pulp, than if it makes a shape change measurement which consists of just one global number per fiber. Thus the processor describes more closely the effects of purposeful or incidental mechanical treatment during pulp processing.

Examples which illustrate embodiments of the present invention were conducted with dyed nylon fibers and a bleached kraft softwood pulp. In one example, dyed nylon fibers were passed through a cell similar to that in FIG. 5 in a system in which the hydraulics, optics and imaging were similar to those shown in FIG. 12, except that the optical system did not use polarizers.

The imaging system was arranged to acquire four sequential images when manually triggered, with the time lag between images adjusted to the flow rate such that a fiber could be followed in its path between the injector exit and the bottom of the imaged region by the four sequential images. The area imaged included the tip of the injector and the area normally imaged. Dyed nylon fibers, 2 mm in length, which is close the mean length of typical softwood pulp fibers, were passed through the imaging area in a water suspension, using a water sheath. Following image acquisition, software superimposed the four images, creating a stop-action record of how a fiber was progressively aligned hydrodynamically, and the superimposed images were printed on a laser printer. The results showed that fibers were hydrodynamically aligned and positioned in the tapered flow region and remained within the jet while they passed through the imaged region.

In another example, bleached kraft softwood fibers were passed at speeds of between 0.5 and 1.0 m/s through a cylindrical cell similar to that in FIG. 5 which has provisions for positioning the injector tip precisely with respect to the cell centerline and using similar hydraulics and optics to those shown in FIG. 12. Tests were carried out with and without polarizing filters, using a commercial high speed video camera and recorder operated at 1000 frames per second. When the video recorder was used, between 5 and 10 seconds of high speed cell operation were recorded, after which the video tape was replayed at a much slower rate, permitting sample jet and fiber behaviour to be studied in slow motion. The sample fluid was dyed with commercial food coloring to permit visualizing it downstream of the injector tip. Using no polarizers, both by direct observation and by high speed video, the high speed sample jet in the imaging region was narrow, laminar and stable. Using polarizing filters, the slow motion video showed that both straight and deformed fibers of all lengths were aligned and positioned to be within the sample jet as they passed through the imaging region. The speeds at which the cell was operated were suitable for industrial use.

In another example, a suspension of a bleached kraft softwood pulp was poured into the reservoir of a system similar to that shown in FIG. 12, using a cell similar to that in FIGS. 1 to 3 or 4, where it was continuously and gently agitated by a slow air bubbler. The sample fluid was dyed with commercial food coloring to permit visualizing it downstream of the injector tip. The sheath and outlet flow regulating valves were adjusted so that laminar conditions existed in the cell and the gravity fed fiber bearing fluid tapered smoothly on exit from the injector, becoming a thin sheet which was centered in the terminal part of the cell. The fiber bearing sheet was seen to be much thinner from the side than the length of typical fibers. Approximately 600 fibers were analyzed for curl index and length which took approximately 20 minutes.

Figure 14A:
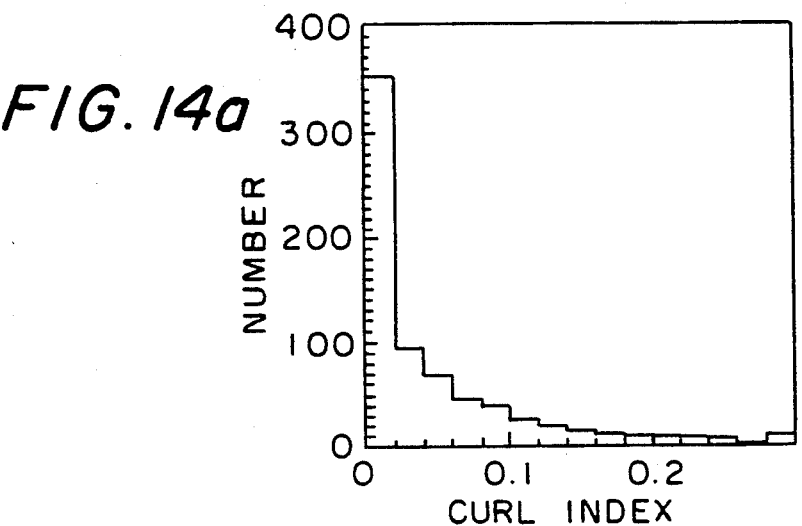
FIGS. 14a to 14f are graphs of experimental tests conducted with an imaging fiber analyzer for typical softwood kraft pulp fiber samples.
Figure 14B:
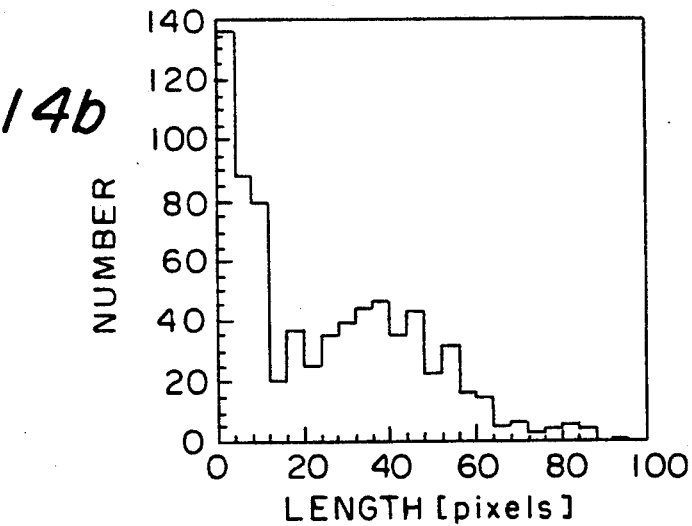
Figure 14C:
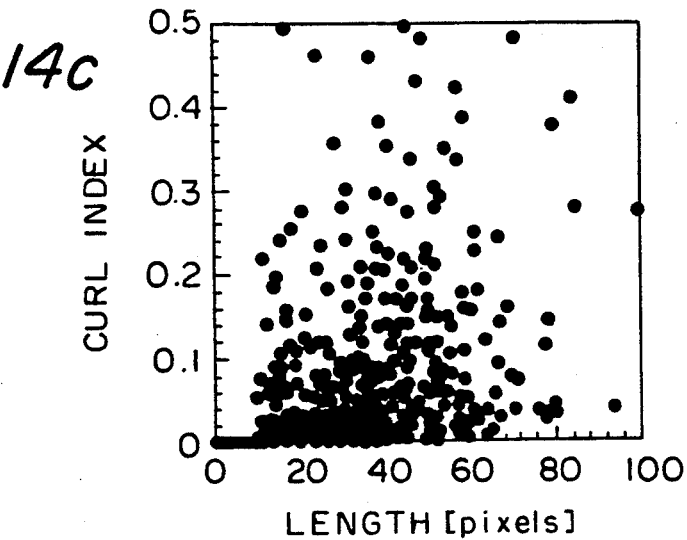

The output data were plotted as separate frequency distributions of curl index and length and are illustrated in FIGS. 14a, 14b and 14c. These results show that the imaging fiber analyzer simultaneously yields fiber length and deformation data rapidly and with minimal or no operator intervention.

Figure 14D:
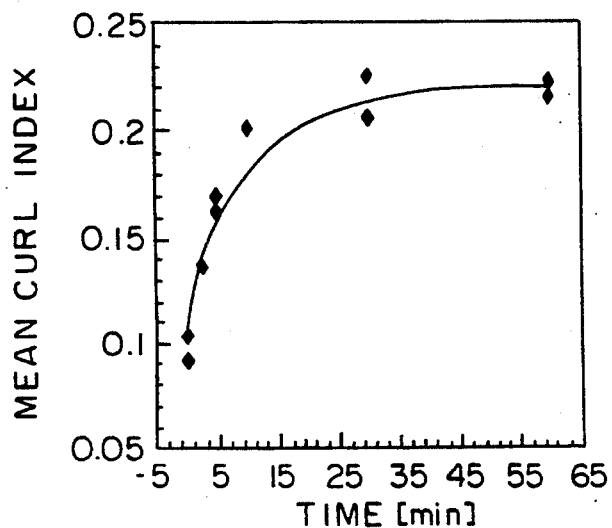
Figure 14E:
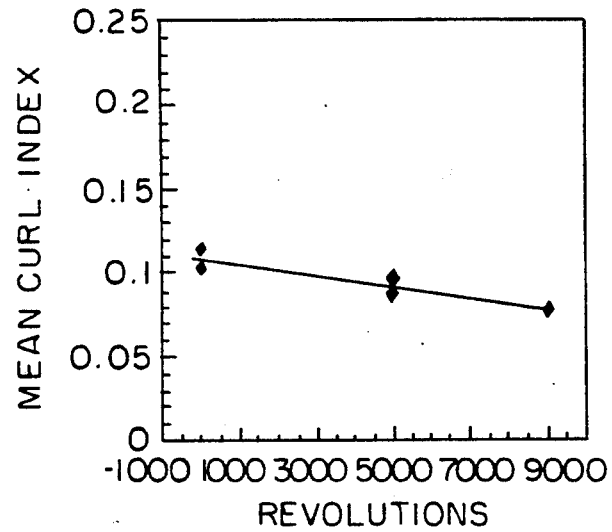
Figure 14F:
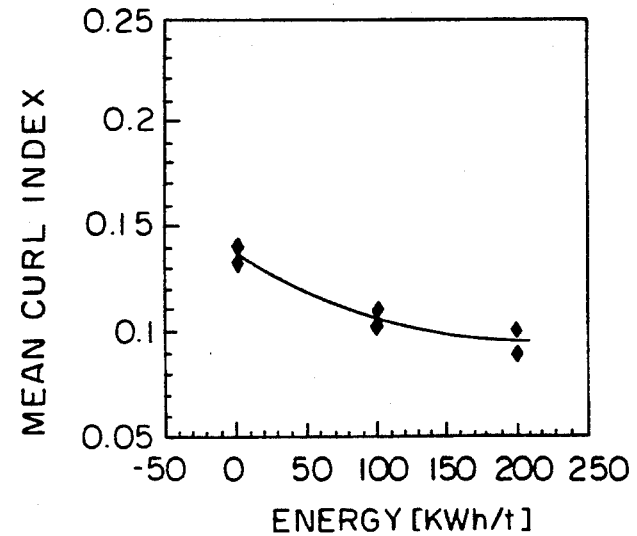

FIG. 14d shows the mean curl index for each sample plotted against time in the Hobart laboratory mixer. FIG. 14e shows a mean curl index versus refining energy for the Escher-Wyss lab refiner run at a specific edge load of 3 W/(m/sec) to specific energies of 200 kWh/Tonne. FIG. 14f shows a mean deformation versus revolutions for the PFI mill for up to 10,000 revolutions. The fiber deformation introduced and removed by these treatments is similar to that reported for commercial laboratory and mill refiners.

In another example, a suspension of a thermomechanical pulp was passed through the same system as in FIG. 12. Despite the lignin on the fibers, the visual contrast with polarizing filters was good, permitting similar measurements to be made as on chemical pulps.

The results show that the imaging fiber analyzer generated fiber deformation data for the effects of mechanical treatment which are comparable to the established method for both chemical and mechanical pulps, and that the between sample repeatability is acceptable.

The embodiments of the present invention in which an exclusive property or privilege is claimed are defined as follows:

1. A fiber analyzer for determining fiber lengths of fibers in a fiber suspension, comprising:
   a flow cell having a first flow passage for a fiber suspension stream with a sheath flow passage about the first flow passage, the first flow passage tapering to an exit aperture connecting with the sheath flow passage to form a combined passage, the combined passage having a reduction in area downstream of the exit aperture to align and position fibers in an elongated stream;
   an imaging area in the cell downstream of the reduction in area in the combined passage, wherein the elongated stream is surrounded by sheath fluid;
   light source to apply light to one side of the imaging area in the cell;
   imaging detector on opposite side of the imaging area to the light source, the imaging detector providing signals representing fiber present in the imaging area, and
   means to process the signals to determine fiber length.

2. The fiber analyzer according to claim 1 wherein the sheath flow passage is coaxial about the first flow passage, the first flow passage having a frusto-conical taper to the exit aperture, the combined passage having a frusto-conical taper downstream of the exit aperture tapering to a reduced area representing the imaging area 3. The fiber analyzer according to claim 1 wherein the first flow passage tapers to a longitudinal slit exit aperture and the sheath flow passage is coaxial about the first flow passage having a circular cross-section, the combined passage having a circular cross-section.

4. The fiber analyzer according to claim 1 wherein the first flow passage tapers to a longitudinal slit exit aperture, and the sheath flow passage is coaxial about the first flow passage having a rectangular cross-section, the combined passage having a rectangular crosssection.

5. The fiber analyzer according to claim 1 wherein a shear area is provided in the imaging area of the combined passage, the imaging detector providing signals representing a fiber present in the imaging area before the shear area and in the shear area, and including means to process the signals to determine fiber length, fiber deformation and fiber flexibility.

6. The fiber analyzer according to claim 5 wherein the shear area occurs in an elbow in the imaging area.

7. The fiber analyzer according to claim 5 wherein the shear area occurs in a T form in the imaging area and including a fluid stream supplied to one arm of the T-form causing the fiber suspension stream to turn.

8. The fiber analyzer device according to claim 1 wherein a first circular polarizing filter is positioned on the one side of the imaging area and a second circular polarizing filter is positioned on the opposite side of the imaging area so that the light source passes through the first circular polarizing filter, the imaging area, and the second circular polarizing filter before being detected by the imaging detector, and wherein the second polarizing filter is in an extinction position with respect to the first polarizing filter.

9. A fiber analyzer device for determining fiber deformation and fiber length in a pulp comprising:
   means to provide a fiber suspension in a liquid;
   a flow cell having a first flow passage for a fiber suspension stream, with sheath fluid flow passages on both sides of the first flow passage, the first flow passage tapering to a slit, an exit aperture connecting with the sheath flow passages to form a combined passage, the combined passage having a reduction in area downstream of the exit aperture to align, position and orient fibers in an elongated planar stream;
   an imaging area in the cell downstream of the reduction in area of the combined passage, wherein the elongated planar stream has sheath fluids on both sides;
   an optical system having an optical axis normal to the elongated planar stream, including a visible light source to apply light to one side of the imaging area of the cell, a first circular polarizing filter on the one side of the imaging area and a second circular polarizing filter on an opposite side of the imaging area, the second polarizing filter being in an extinction position with respect to the first polarizing filter,
   an imaging detector on the opposite side of the imaging area to detect fibers in the imaging area imaged from the light source and through the polarizing filters, the imaging detector providing signals representing fiber presence in the imaging area, and
   means to process the signals to determine fiber deformation and fiber length.

10. The fiber analyzer according to claim 9 including a shear area in the imaging area and wherein the imaging detector provides a plurality of signals representing a fiber image at different positions passing in the sample stream through the imaging area, including means to compare the plurality of signals to provide an indication of fiber flexibility.

11. The fiber analyzer according to claim 9 wherein the flow cell has a first flow passage with a rectangular cross-section.

12. The fiber analyzer according to claim 11 wherein the first flow passage has tapering sides to a longitudinal slit forming the exit aperture, the tapering sides having knife type edges at the longitudinal slit.

13. The fiber analyzer according to claim 9 wherein the sheath fluid flow passages have a 1 cross-sectional area than the cross-sectional area of the exit aperture.

14. The fiber analyzer according to claim 9 including a condenser in the optical system for supplying light uniformly to the imaging area.

15. The fiber analyzer according to claim 9 including a lens in the optical system to focus fiber images onto a two dimensional imaging detector.

16. The fiber analyzer according to claim 9 wherein the imaging detector has a shutter means for stop motion imaging.

17. A method of determining fiber length for fibers in suspension comprising the steps of:
- passing a fiber suspension stream through a sheath type flow cell wherein the fiber suspension stream is injected into a sheath fluid stream to align and position fibers and form an elongated combined stream;
- projecting a light from one side of the combined stream;
- collecting images of fibers in the combined stream on an opposite side from the light and producing signals representative of fiber images, and
- processing the signals to determine fiber length.

18. The method of determining fiber length according to claim 17 wherein the fiber suspension stream is injected into the center of the sheath fluid stream through a rectangular slit to form an elongated planar fiber suspension stream in the combined stream, the combined stream passing through a tapered section of the flow cell into an imaging area where the images of fibers are collected.

19. The method of determining fiber length according to claim 18 wherein the combined stream passes through a shear area in the imaging area and wherein fiber images are collected before and while passing through the shear area to produce signals, and wherein the signals are processed to determine fiber flexibility.

20. The method of determining fiber length according to claim 17 wherein circular polarizing filters are provided one on each side of the sheath fluid stream through which the light projects, one filter being in an extinction position with respect to the other filter.

21. A method of determining fiber deformation and fiber length in a pulp comprising the steps of:
- forming a fiber suspension stream with fibers aligned, positioned and oriented;
- passing the fiber suspension stream through an imaging area in a flow cell with an elongated planar shape with sheath fluids on both sides of the fiber suspension stream to form a combined stream;
- projecting a light with an optical axis normal to the combined stream, through a first polarizing filter, the imaging area followed by a second polarizing filter, the second polarizing filter being in an extinction position with respect to the first polarizing filter, and onto an imaging detector to image fibers in the imaging area and produce signals representative of the fibers, and
- processing the signals from the imaging detector to determine fiber deformation and fiber length.

22. The method of determining fiber deformation and fiber length according to claim 21 wherein the imaging area has a shear area therein so fibers passing through the shear area are deformed, obtaining a plurality of images on the imaging detector and producing signals representing fibers before entering the shear area and moving through the shear area;
- processing the signals representing the fibers, and
- comparing shapes of the fibers moving through the shear area to provide an indication of fiber flexibility and flexibility distribution.

23. The method of determining fiber deformation and fiber length according to claim 22 wherein stop motion imaging of the fibers provides a plurality of images representing fibers moving through the shear area.

24. The method of determining fiber deformation and fiber length according to claim 21 wherein the sheath fluids flow faster than the fiber suspension stream prior to the imaging area.

25. The method of determining fiber deformation and fiber length according to claim 21 wherein the fiber suspension stream flows through a longitudinal slit and the sheath fluids join the fiber suspension stream on both sides of the longitudinal slit.

* * * * *

UNITED STATES PATENT AND TRADEMARK OFFICE
CERTIFICATE OF CORRECTION

PATENT NO. : 5,311,290
DATED : May 10, 1994
INVENTOR(S) : James A. OLSON et al.

It is certified that error appears in the above-indentified patent and that said Letters Patent is hereby corrected as shown below:

Title Page: Item (75) Inventors:

Insert -- A. -- after James

MODES FOR CARRYING OUT THE INVENTION: Column 6, Line 49:

Delete "c" after 6 and insert -- 0 --

Column 7, Line 31:

Change "are" to -- area --

Column 7, Line 54:

Delete "desertion" and insert --description--

Claim 4, Column 9, Line 55: reads . . .

"cros-" Should read . . . cross-

Claim 13, Column 10, Line 58: Delete "1" and insert --larger--

Signed and Sealed this

Twenty-seventh Day of September, 1994

Attest:

BRUCE LEHMAN

Attesting Officer     Commissioner of Patents and Trademarks